United States Patent

Schmitt

[11] Patent Number: 5,883,937
[45] Date of Patent: Mar. 16, 1999

[54] X-RAY DIAGNOSTIC APPARATUS

[75] Inventor: Thomas Schmitt, Forchheim, Germany

[73] Assignee: Siemens Aktiengesellschaft, Munich, Germany

[21] Appl. No.: 893,514

[22] Filed: Jul. 11, 1997

[30] Foreign Application Priority Data

Jul. 12, 1996 [DE] Germany .................. 196 28 245.4

[51] Int. Cl.⁶ .................................................. H01J 31/49
[52] U.S. Cl. ........................... 378/189; 378/98.8; 378/37
[58] Field of Search .............................. 378/37, 189, 98.8

[56] References Cited

U.S. PATENT DOCUMENTS

| | | |
|---|---|---|
| 4,259,585 | 3/1981 | Novak et al. . |
| 4,807,273 | 2/1989 | Haendle . |
| 5,079,426 | 1/1992 | Antonuk et al. . |
| 5,148,460 | 9/1992 | Aichinger ................................. 378/37 |
| 5,327,890 | 7/1994 | Matura et al. . |
| 5,369,268 | 11/1994 | Van Aller et al. . |

FOREIGN PATENT DOCUMENTS

| | | |
|---|---|---|
| OS 39 01 495 | 8/1989 | Germany . |
| PS 195 06 810 | 6/1996 | Germany . |
| WO 96/03077 | 2/1996 | WIPO . |

OTHER PUBLICATIONS

Siemens Brochure for "VERTIX U, Universelles Röntgenaufnahmegerät".

*Primary Examiner*—Craig E. Church
*Attorney, Agent, or Firm*—Hill & Simpson

[57] ABSTRACT

An X-ray diagnostic apparatus has at least one radiation transmitter and at least one radiation receiver arranged spaced therefrom and an examination subject support plate. The radiation receiver is fashioned as a matrix detector and extends over the entire area of the examination subject support plate. Such an X-ray diagnostics apparatus is simply constructed in terms of structure and supplies high-contrast X-ray exposures in a short time and with low radiation exposure.

16 Claims, 5 Drawing Sheets

X-RAY DIAGNOSTIC APPARATUS

BACKGROUND OF THE INVENTION

1. Field of the Invention

The present invention is directed to an X-ray diagnostic apparatus with at least one radiation transmitter and at least one radiation receiver arranged spaced therefrom as well as with a examination subject support plate, wherein the radiation receiver is fashioned as matrix detector.

2. Description of the Prior Art

An X-ray detector of the above type is disclosed, for example, in U.S. Pat. No. 5,079,426. In this known apparatus, a radiation detector fashioned as a matrix detector is immovably arranged under a examination subject support plate of the X-ray diagnostic apparatus.

Further, German OS 195 06 810 discloses an X-ray examination apparatus for X-ray slit exposure technology having a radiation detector is fashioned as a matrix detector, but the arrangement of the matrix detector in the X-ray examination apparatus is not described.

PCT Application WO 96/03077 discloses a method for registering X-ray images as well as an examination subject support means with a examination subject support plate. The examination subject support means has a longitudinally and transversely displaceable X-ray receiver that can be fashioned as a matrix detector. In the examination subject support means of PCT Application WO 96/03077, whole-body exposures or large-area X-ray exposures, for example examinations of the leg vessels, require a relatively large amount of time because of the displacement of the matrix detector required therefor. Moreover, overlapping exposures can occur in the adjustment of the radiation receiver, leading to an undesirable radiation exposure in the overlap region.

U.S. Pat. No. 5,369,268 discloses a matrix detector that has a sensor surface of amorphous selenium.

The Siemens brochure "Vertix U—Universelles Röntgenaufnahmegeratt", order number A91001-M1024-G241-04, also discloses an X-ray diagnostic apparatus wherein the radiation receiver is fashioned as a catapult screen compartment. A film cassette can be inserted into the catapult screen compartment. The film arranged behind a screen plate is exposed by the incident X-rays. High costs arise due to the employment of films for the registration of the X-ray image. Moreover, the required film developing represents a certain environmental pollution. Moreover, an electronic evaluation of the image signals is also not possible given this X-ray diagnostics apparatus.

SUMMARY OF THE INVENTION

An object of the present invention is to provide a structurally simply constructed X-ray diagnostics apparatus that supplies high-contrast X-ray exposures in a short time and with low radiation exposure.

In an X-ray diagnostics apparatus with at least one radiation transmitter and at least one radiation receiver arranged spaced therefrom as well as with a examination subject support plate, wherein the radiation receiver is fashioned as matrix detector, this object is inventively achieved by the matrix detector (also referred to as a solid-state detector) being co-extensive in area with the entire examination subject support plate. The areas of the matrix detector and the support plate which are co-extensive are in planes (or troughs if the support plate is trough-shaped) parallel to the c.—c. axis of a patient on the support plate.

No positioning of the matrix detector is required given the inventive X-ray diagnostics apparatus since this matrix detector extends substantially over the entire examination subject support plate. The time expended for a single X-ray exposure is thereby significantly reduced. Given large-area X-ray exposures that are required, for example, in the examination of the leg vessels, overlap regions are avoided in the X-ray exposures, so that, in addition to the low time outlay, the radiation exposure also is correspondingly low.

In an embodiment of the invention the examination subject support plate can be radiation-transparent and the matrix detector then can be arranged at the underside of the radiation-transparent examination subject support plate. As a result of its compact structure and its low weight, the matrix detector can also be integrated into the examination subject support plate in a simple way. According to a further embodiment of the invention, the matrix detector forms at least a part of the examination subject support plate. The examination subject support plate can be fashioned flat or trough-shaped in all embodiments within the scope of the invention.

The sensor surface of the matrix detector facing toward the radiation transmitter is preferably composed of amorphous silicon or of amorphous selenium.

Due to the small dimensions and the low weight, the matrix detector is also suitable for an X-ray diagnostic apparatus wherein the examination subject support plate can be folded over and thereby used as a screen wall.

The small dimensions and the low weight also enable the integration of the matrix detectors in X-ray diagnostics apparatus that has a C-arm for the radiation transmitter and the radiation receiver as well as in a mammography examination apparatus as well as in an apparatus for tomogram and figure radiology. In an apparatus for tomogram and figure radiology, for example, spiral, elliptical, circular or linear scans can be achieved in the X-ray exposure due to the opposed adjustability of the radiation transmitter and the matrix detector. Slice figures can thus be produced for various subject presentations (for example, skull and joints as well as spinal column, gall bladder, kidney and lung).

In an embodiment wherein the matrix detector has at least one flexibly fashioned sensor surface, then the sensor surface comes directly into contact with the patient at nearly all locations of the body. An improvement of the image quality is thereby achieved.

Electronic evaluation of the image signals given a matrix detector as the radiation receiver is facilitated when the image signals can be can be electronically stored. This is particularly simple in the inventive X-ray apparatus in an embodiment wherein the apparatus itself includes a memory for storing the image signals. A further simplification in the use of the inventive X-ray diagnostics apparatus is achieved by the integration of a unit for reading out stored patient data and/or image signals from the memory. For example, a magnetic card or chip card can serve as a memory medium, with a card write/read unit being provided for reading the data in or out. Advantageously, the memory for storing the image signals and/or the unit for readout from the memory can be integrated in the matrix detector.

According to an advantageous exemplary embodiment, the inventive X-ray diagnostics apparatus can also include a receiver for voice input as well as a memory for storing voice inputs. It is thus possible that the physician can directly undertake and store his/her diagnosis during the X-ray exposure or when evaluating the X-ray image.

DESCRIPTION OF THE PREFERRED EMBODIMENTS

Figure 1:
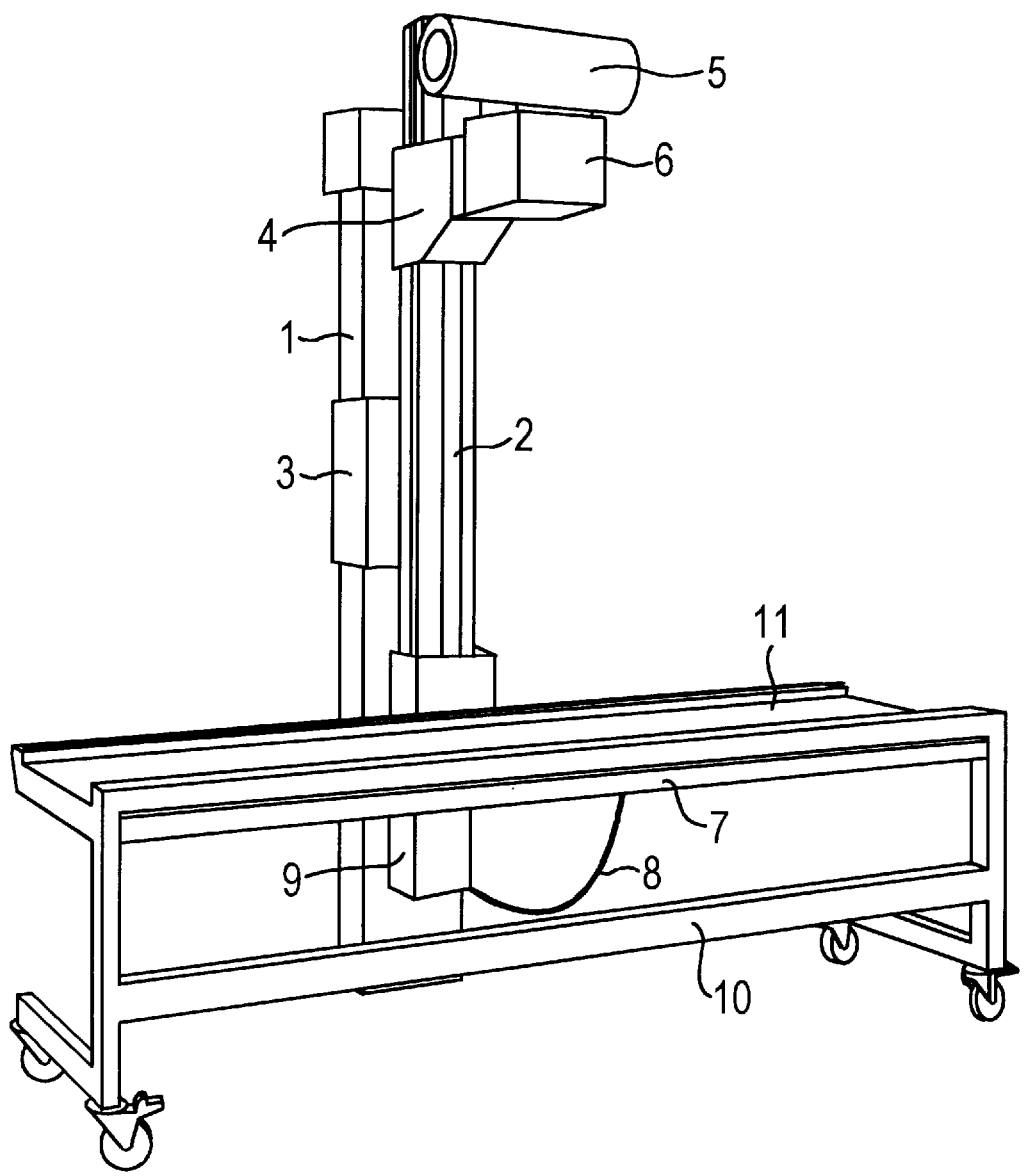
FIG. 1 shows a first embodiment of the inventive X-ray diagnostics apparatus.

The apparatus shown in FIG. 1, has a stand 1 at which a swivel arm 2 is rotatably held with a lockable swivel device. A radiation transmitter 4, which includes an X-radiator 5 and a radiation diaphragm 6, is arranged at one side of the swivel arm 2. The radiation transmitter 4 can be longitudinally displaced and inclined and can also be locked in a selected position. The exemplary embodiment of the inventive X-ray diagnostics apparatus shown in FIG. 1 further has a movable examination subject support arrangement 10 with a radiation-transparent examination subject support plate 11. X-rays emitted by the radiation transmitter 4 are acquired by a radiation receiver that is fashioned as a matrix detector 7. In the embodiment shown in FIG. 1, the matrix detector 7 is arranged under the radiation-transparent examination subject support plate 11 and extends over essentially the entire area of the examination subject support plate 11, i.e., it is co-extensive therewith. The matrix detector 7 is connected to an electronics unit 9 via an electronics cable 8. Only the voltage supply of the matrix detector 7 ensues via the electronics cable 8 in the illustrated exemplary embodiment. Storage of the image signals ensues in a memory that is integrated in the matrix detector 7 in the embodiment shown in FIG. 1.

When the examination subject support arrangement 10 is pushed in, the radiation-transparent examination subject support plate 11 is arranged in the beam path between the radiation transmitter 4 and the matrix detector 7. Examinations of a prone or supine patient or a patient lying on his or her side are thus possible from head to foot.

Within the scope of the invention, the matrix detector 7 can also be integrated in the examination subject support plate 11 or the matrix detector 7 can form at least a part of the examination subject support plate 11 instead of the radiation-transparent examination subject support plate 11 with the matrix detector 7 arranged at its underside.

Instead of a portable examination subject support arrangement 10 as in the illustrated version, the X-ray diagnostic apparatus shown in FIG. 1 can have a stationary examination subject support arrangement with a radiation-transparent examination subject support plate which can be swivelled out of a horizontal position into a vertical position. The folded-over, radiation-transparent examination subject support plate can then be used as screen wall.

A further modification (not shown in FIG. 1) allows slice and figure radiology. To this end, the radiation transmitter 4 is arranged so as to be longitudinally and/or transversely displaceable at a ceiling rail system, for example via a telescope-like mount. In addition to being adjustable in height, the radiation transmitter 4 can be inclined. This embodiment also has a two-dimensionally adjustable examination subject support plate (referred to as a "floating table top") that can in turn be fashioned in any of the above-described ways. The radiation transmitter 4 and the matrix detector 7 are thus adjustable opposite one another in a spiral, circular, elliptical or linear direction.

Figure 2:
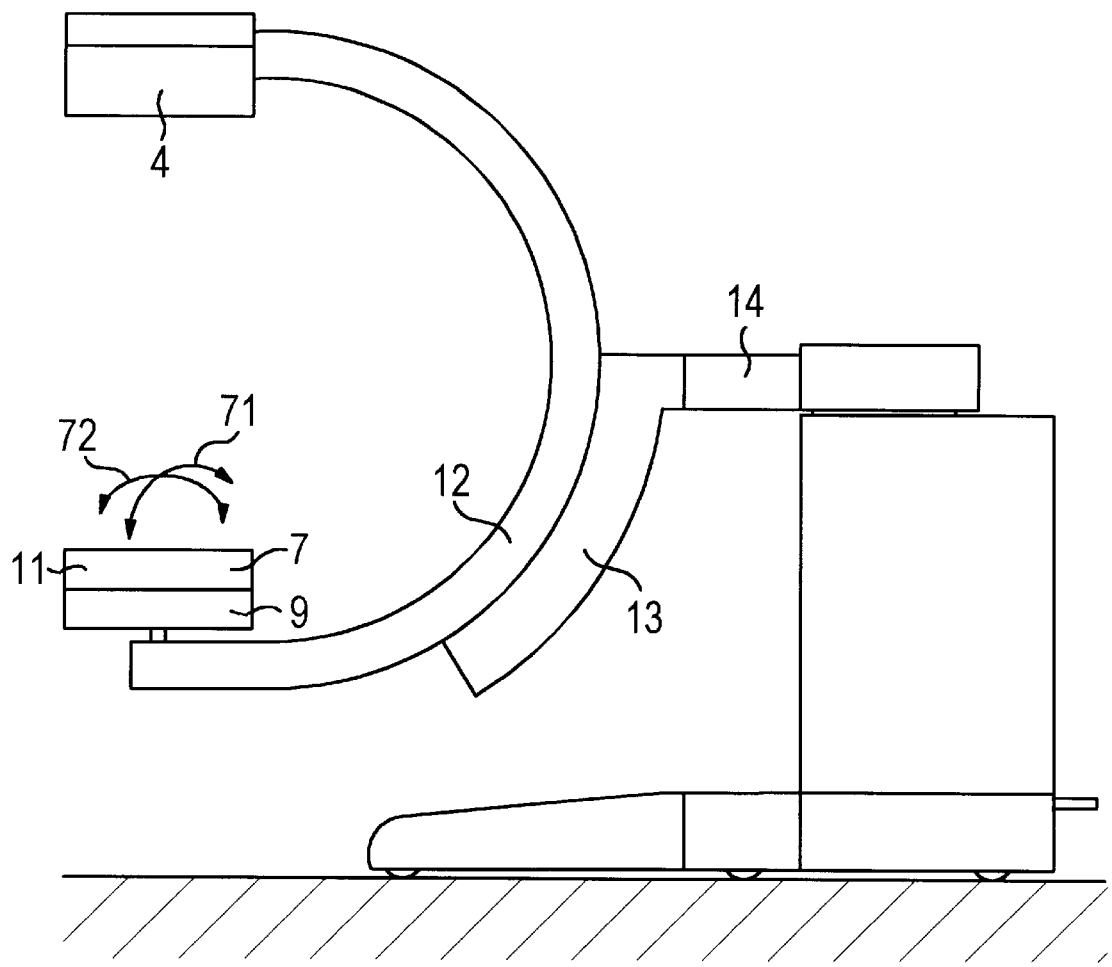
FIG. 2 shows a second embodiment of the inventive X-ray diagnostics apparatus.

FIG. 2 shows a portable X-ray diagnostic apparatus that has a C-arm 12. The radiation transmitter 4 is arranged at the upper end of the C-arm 12 and the matrix detector 7 with its electronics unit 9 is arranged at the lower end of the retainer arm 12. The C-arm 12 is guided along a circular segment-shaped carrier 13. In the illustrated exemplary embodiment, the carrier 13 is rotatable around an axis 14. As a result, the radiation receiver 7 and the radiation transmitter 4 lying thereabove can be brought into the desired position in a simple way. In this exemplary embodiment, the matrix detector 7 forms the examination subject support plate 11 (and thus the matrix detector 7 and the examination subject support plate 11 are co-extensive) that can be inclined in the directions shown by the arrows 71 and 72.

Figure 3:
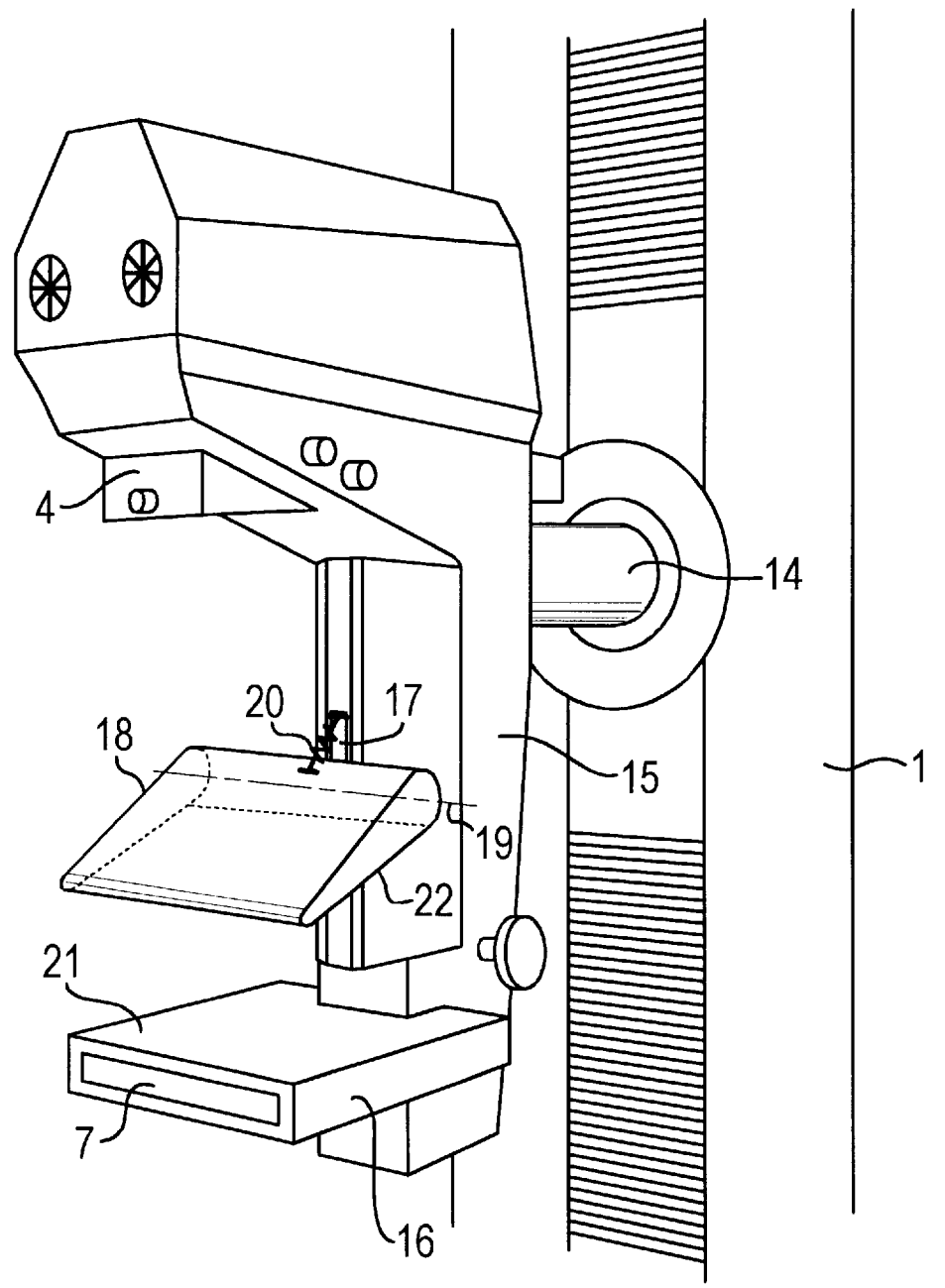
FIG. 3 shows a third embodiment of the inventive X-ray diagnostics apparatus.
Figure 4:
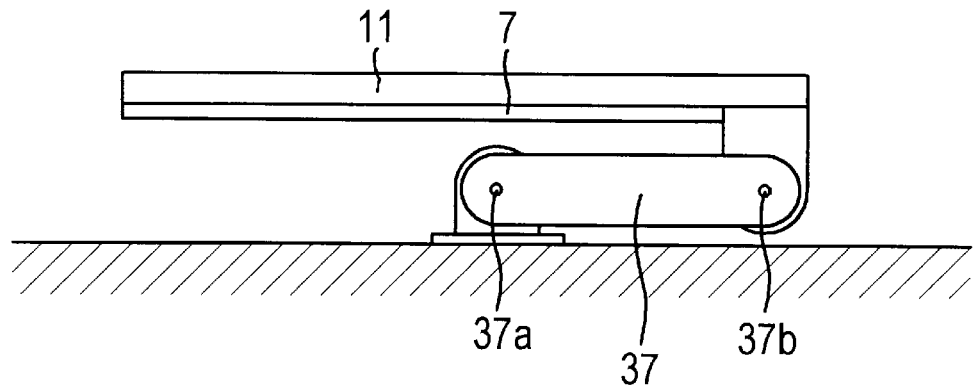
FIGS. 4–7 show a further embodiment of the inventive X-ray diagnostics apparatus in various positions.
Figure 5:
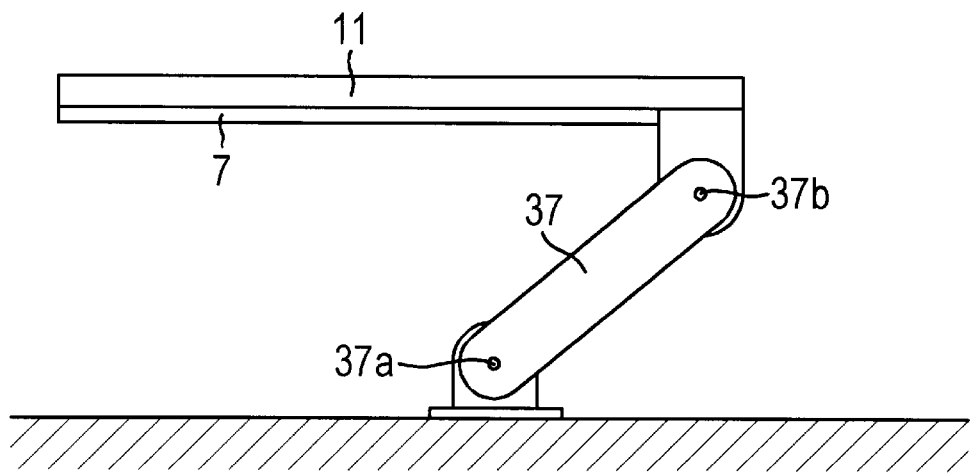
Figure 6:
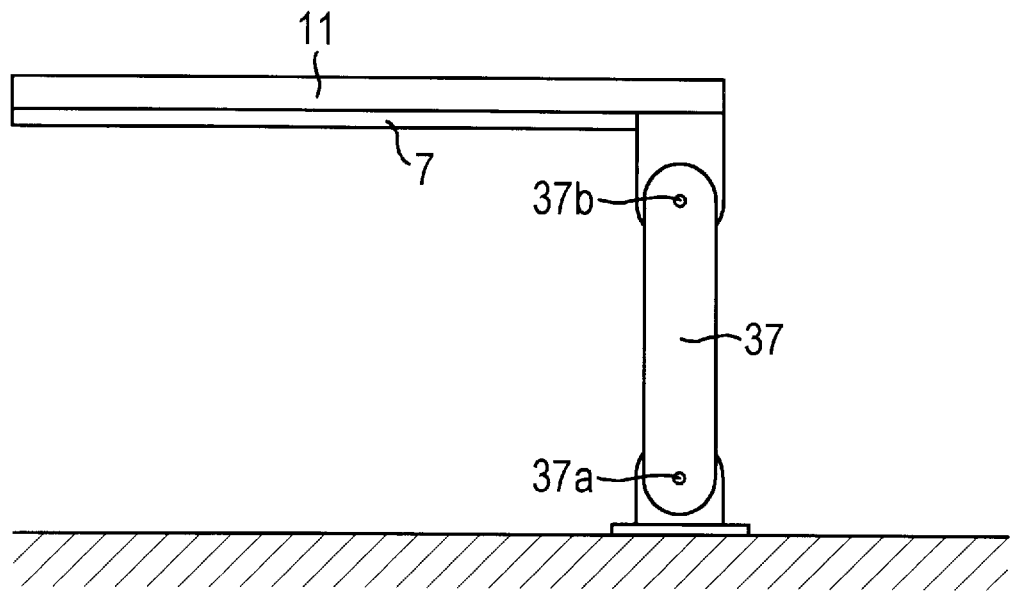

FIG. 3 shows an X-ray diagnostic apparatus for mammography exposures. This apparatus has a stand 1 at which a holder 15, pivotable around an axle 14, is seated so as to be height-adjustable via this axle 14. The holder 15 carries the radiation transmitter 4 at its upper end and a examination subject support plate 16 in which a matrix detector 7 is integrated at its lower end. The examination subject support plate 16 and the matrix detector 7 are co-extensive in area.

A motor-adjustable compression carriage 17 at which a compression plate 18 is height-adjustably seated is arranged in the holder 15. This compression plate 18 can be pivoted around a horizontal axis 19 against the force of a spring element 20. As can be seen from FIG. 3, the space between the examination subject support plane 21 of the examination subject support plate 16 and the compression surface 22 of the compression plate 18 tapers toward the patient-proximate side. After a female breast is placed onto the examination subject support plane 21, the compression plate 18 is adjusted in the direction toward the examination subject support plate 16 via the compression carriage 17 for compression thereof.

In the illustrated exemplary embodiment of the inventive X-ray diagnostics apparatus, the matrix detector 7 is integrated in the examination subject support plate 16 and the examination subject support plane 21 of the examination subject support plate 16 is radiation-transparent. Alternatively, the sensor surface of the matrix detector 7 can form the examination subject support plane 21—in this case, the matrix detector 7 then forms the examination subject support plate 16.

Figure 7:
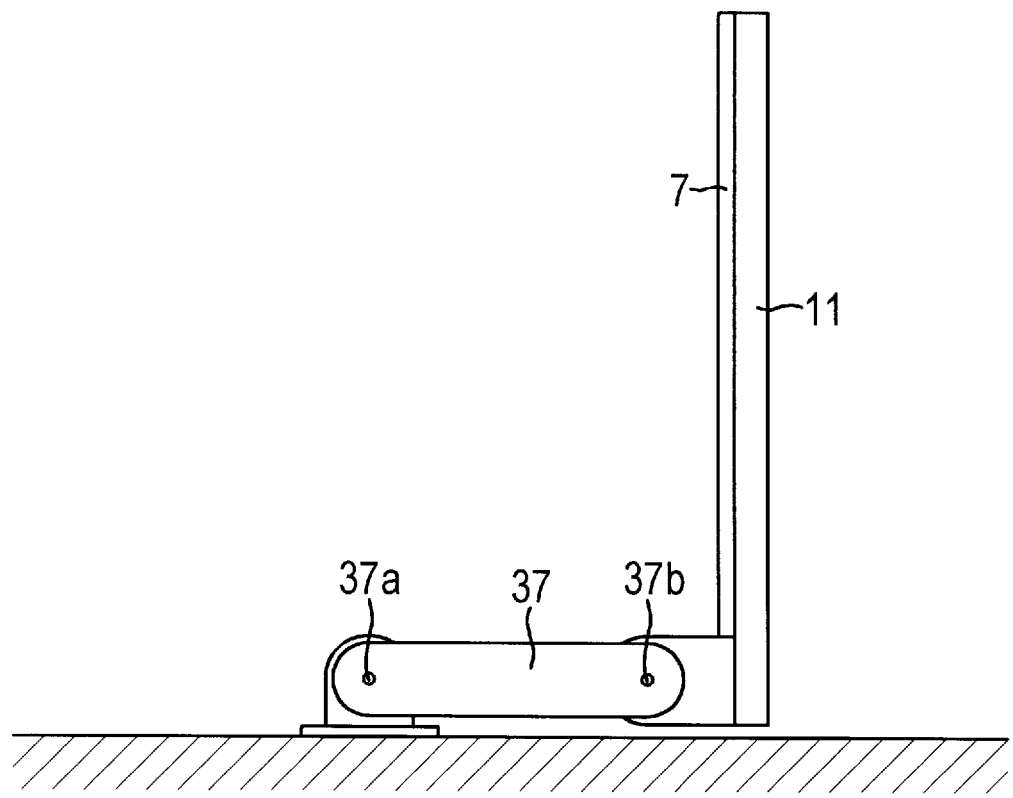

A preferred embodiment of the inventive X-ray diagnostics apparatus is shown in FIGS. 4 through 7. The X-ray diagnostics apparatus again has a radiation-transparent examination subject support plate 11 with a matrix detector 7 arranged beneath it that extends over the entire area of the radiation-transparent examination subject support plate 11. By means of a swivel foot 37 has a respective rotational axes 37a and 37b at its two ends, the radiation-transparent examination subject support plate 11 can be adjusted with infinite variation from its lowest horizontal position (FIG. 4) into horizontal positions (FIGS. 5 and 6) of various heights. Further, the examination subject support plate 11 can be pivoted from the positions shown in FIGS. 4 through 6 into a vertical position (FIG. 7). The matrix detector 7 is then arranged at the back side of the radiation-transparent examination subject support plate 11. In the positions according to FIGS. 5 and 6, the radiation-transparent examination subject support plate 11 can also be brought into a slanted position by swivelling around the horizontal rotational axis 37b. The position of the radiation-transparent examination subject support plate 11 can thus be optimally matched to the particular examination.

Although modifications and changes may be suggested by those skilled in the art, it is the intention of the inventor to embody within the patent warranted hereon all changes and modifications as reasonably and properly come within the scope of his contribution to the art.

I claim as my invention:

1. An X-ray diagnostic apparatus comprising:

a radiation transmitter;

a radiation receiver disposed a distance from said radiation transmitter;

an examination subject support plate disposed between said radiation transmitter and said radiation receiver; and said radiation receiver comprising a matrix detector which generates image signals which, in combination, form an image of an examination subject, said matrix detector being co-extensive in area with said support plate.

2. An X-ray diagnostic apparatus as claimed in claim 1 wherein said support plate is comprised of radiation-transparent material, and wherein said matrix detector is disposed at a side of said support plate facing away from said radiation transmitter.

3. An X-ray diagnostic apparatus as claimed in claim 1 wherein said matrix detector is integrated in said support plate.

4. An X-ray diagnostic apparatus as claimed in claim 1 wherein said matrix detector comprises at least a portion of said support plate.

5. An X-ray diagnostic apparatus as claimed in claim 1 wherein said matrix detector has at least one sensor surface comprised of amorphous silicon.

6. An X-ray diagnostic apparatus as claimed in claim 1 wherein said matrix detector has at least one sensor surface comprised of amorphous selenium.

7. An X-ray diagnostic apparatus as claimed in claim 1 further comprising means for pivoting said support plate between a horizontal position and a vertical position.

8. An X-ray diagnostic apparatus as claimed in claim 1 further comprising a C-arm having opposite ends at which said radiation transmitter and said matrix detector are respectively mounted, and a carrier for said C-arm having a guide comprising a circular segment in which said C-arm is movable.

9. An X-ray diagnostic apparatus as claimed in claim 1 further comprising a compression plate disposed above said support plate and means for moving said compression plate toward said support plate for compressing a portion of an examination subject between said compression plate and said support plate.

10. An X-ray diagnostic apparatus as claimed in claim 1 wherein said matrix detector comprises at least one flexible sensor surface.

11. An X-ray diagnostic apparatus as claimed in claim 1 further comprising means for adjusting a distance between said radiation transmitter and said matrix detector.

12. An X-ray diagnostic apparatus as claimed in claim 1 further comprising memory means for storing said image signals.

13. An X-ray diagnostic apparatus as claimed in claim 12 wherein said memory means comprises a card.

14. An X-ray diagnostic apparatus as claimed in claim 13 further comprising a card read/write unit for reading data into and from said card.

15. An X-ray diagnostic apparatus as claimed in claim 12 further comprising means for reading data into and from said memory means.

16. An X-ray diagnostic apparatus as claimed in claim 1 further comprising means for receiving a voice input, and means for storing said voice input.

* * * * *